US00PP32644P2

(12) United States Plant Patent
O'Connell

(10) Patent No.: US PP32,644 P2
(45) Date of Patent: Dec. 15, 2020

(54) ***ALOE* PLANT NAMED 'CRIMSON DRAGON'**

(50) Latin Name: ***Aloe* hybrid**
Varietal Denomination: CRIMSON DRAGON

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/873,318

(22) Filed: Mar. 17, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Cassandra Bright

(57) ABSTRACT

A new and distinct cultivar of *Aloe* plant named 'CRIMSON DRAGON' is disclosed, characterized by rosettes of slightly recurved slate-green leaves overlaid with an intricate network of reticulate, truncate tuberculate papillae of a frosty mint overlaid by nearly iridescent intense crimson and bright crimson margins. The overall crimson color is exceptionally bright and ornamental. Plants offset freely, forming a cluster quickly and growing larger than many comparable color miniature *Aloes*. *Aloe* 'Crimson Dragon' has exhibited resistance to the *Eriophyid* mite (*Aloe* mite), whereas many of the comparable colorful miniature *Aloes* are prone to deformation from the *Eriophyid* mite. The new variety is an *Aloe*, typically produced as a garden or container plant.

2 Drawing Sheets

Figure 1:
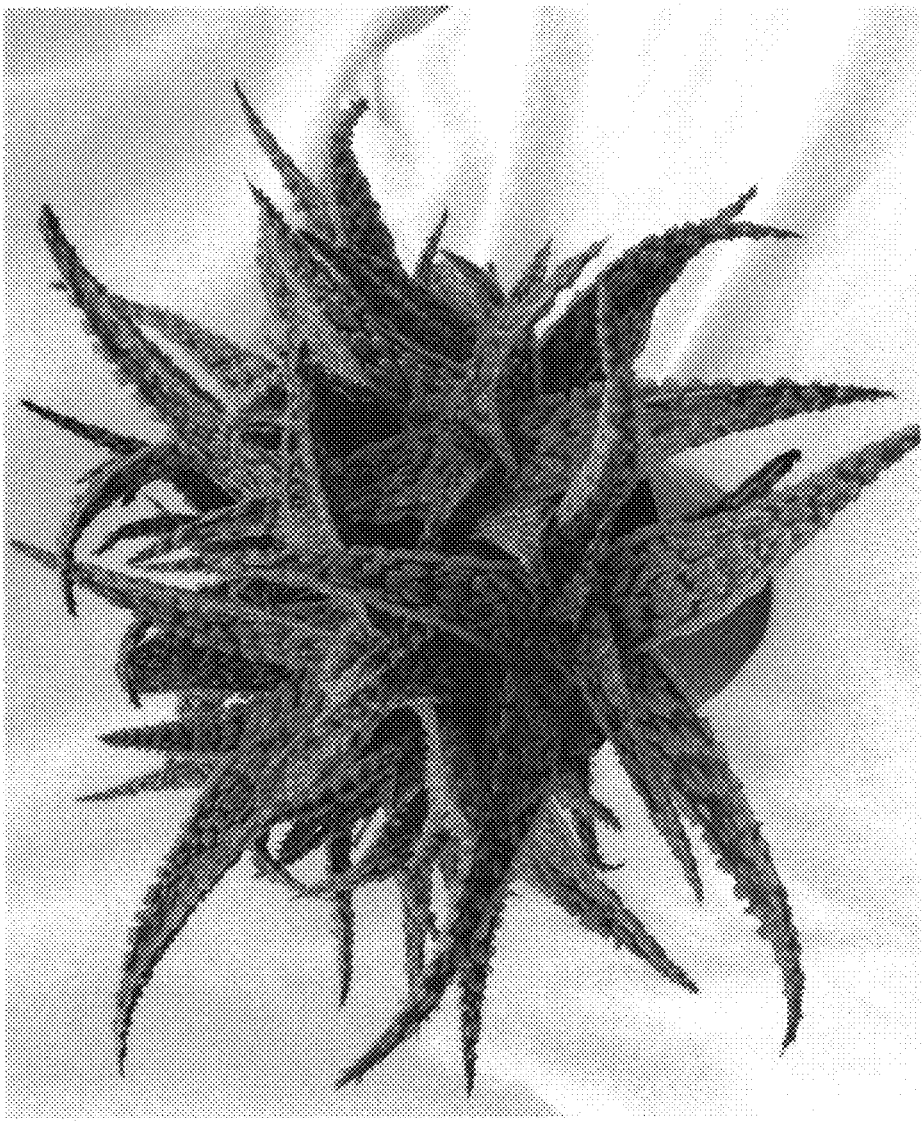

Latin name of the genus and species: *Aloe* hybrid.
Variety denomination: 'CRIMSON DRAGON'.

BACKGROUND OF THE INVENTION

The new cultivar is a product of a planned breeding program. The seed parent is the unpatented proprietary *Aloe* hybrid 'ERT 03'. The pollen parent is the unpatented proprietary *Aloe* hybrid 'Red Des'. The crossing was made in September 2014 at a commercial greenhouse in Vista, Calif. 'CRIMSON DRAGON' was selected by the inventor in August 2015.

Asexual reproduction of the new cultivar 'CRIMSON DRAGON' was first performed by tissue culture at a commercial laboratory in Vista, Calif. in September 2015. 'CRIMSON DRAGON' has since produced several generations and has shown that the unique features of this cultivar are stable and reproduced true to type.

SUMMARY OF THE INVENTION

The cultivar 'CRIMSON DRAGON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CRIMSON DRAGON.' These characteristics in combination distinguish 'CRIMSON DRAGON' as a new and distinct *Aloe* cultivar:

1. *Aloe* 'Crimson Dragon' produces rosettes of slightly recurved glaucous slate green leaves, overlaid by an intricate network of reticulate, truncate tuberculate papillae of a frosty mint overlaid by nearly iridescent intense crimson, and further accentuated with wide bright crimson margins. Margins are strongly variable, often slightly truncate dentate to continuously dentate.
2. *Aloe* 'Crimson Dragon' displays more of an overall glowing crimson color than other similar small *Aloes*.
3. *Aloe* 'Crimson Dragon' offsets freely to produce an attractive, faster growing cluster.
4. *Aloe* 'Crimson Dragon' grows somewhat larger than many of the popular new colorful miniature *Aloes*.
5. *Aloe* 'Crimson Dragon' has exhibited resistance to the *Eriophyid* mite (*Aloe* Mite), whereas many of the comparable colorful miniature *Aloes* are prone to deformation from the *Eriophyid* mite.

PARENTAL COMPARISON

Plants of the new cultivar 'CRIMSON DRAGON' are similar to the seed parent in most horticultural characteristics. However, plants of the new variety differ from the seed parent in the following:

1. *Aloe* 'Crimson Dragon' displays a reticulate, tuberculate leaf texture, whereas the seed parent *Aloe* 'ERT 03' exhibits a more papillate leaf texture.
2. *Aloe* 'Crimson Dragon' displays a vivid crimson overlay of the reticulate, tuberculate texture, whereas the papillate texture of *Aloe* 'ERT 03' displays a root beer color overlay.
3. The *Aloe* 'ERT 03' produces offsets, but less in quantity than *Aloe* 'Crimson Dragon', which is freely offsetting to produce attractive clusters.
4. The new *Aloe* 'Crimson Dragon' is nearly acaulescent, whereas *Aloe* 'ERT 03' is more morphologically caulescent.

Plants of the new cultivar 'CRIMSON DRAGON' are similar to the pollen parent in most horticultural characteristics. However, plants of the new variety differ in the following:

1. *Aloe* 'Crimson Dragon' exhibits a more reticulate tuberculate leaf texture than does than does the pollen parent *Aloe* 'Red Des'.
2. *Aloe* 'Crimson Dragon' displays a vivid crimson overlay of the reticulate, tuberculate texture, whereas the less pronounced leaf texture of *Aloe* 'Red Des' displays only a dull reddish blush and is devoid of the vivid crimson color.
3. The *Aloe* 'Red Des' is not prone to much offsetting, whereas *Aloe* 'Crimson Dragon' is freely offsetting to produce attractive clusters.
4. The new *Aloe* 'Crimson Dragon' displays a robust, moderately rapid growth rate, whereas *Aloe* 'Red Des' grows more slowly.
5. *Aloe* 'Crimson Dragon' displays strongly variable dentate margins of vivid crimson, whereas the pollen parent *Aloe* 'Red Des' displays a more evenly denticulate reddish margin.

COMMERCIAL COMPARISON

'CRIMSON DRAGON' can be compared to the unpatented commercial variety *Aloe* 'Christmas Sleigh'. The two *Aloe* varieties are similar in most horticultural characteristics; however, the new variety differs in the following:

1. *Aloe* 'Crimson Dragon' exhibits a strongly variable, often truncately dentate to continuously dentate margin of crimson, whereas *Aloe* 'Christmas Sleigh' displays a slightly longer, evenly doubly dentate margin of crimson.
2. *Aloe* 'Crimson Dragon' grows more robustly to a larger rosette size than does *Aloe* 'Christmas Sleigh', which is more of a miniature *Aloe*.
3. *Aloe* 'Crimson Dragon' displays a reticulate, tuberculate, prominently elevated leaf texture, whereas *Aloe* 'Christmas Sleigh' exhibits an occasional papillate protuberance on the leaf surface.
4. *Aloe* 'Crimson Dragon', due to the reticulate, tuberculate leaf texture, covering much of the surface of the leaf, appears to have a glowing overlay of crimson, whereas *Aloe* 'Christmas Sleigh' does not exhibit the colorful overlay of crimson; displaying only a largely slate blue-green leaf color, with a few reddish papillae and red dentate margins.

'CRIMSON DRAGON' can also be compared to the unpatented commercial variety *Aloe* 'Lizard Lips.' The two *Aloe* varieties are similar in most horticultural characteristics; however, the new variety differs in the following:

1. *Aloe* 'Crimson Dragon' produces rosettes comprised of leaves with a reticulate, tuberculate texture covering much of the surface of the leaf, overlaid with a vivid crimson, whereas *Aloe* 'Lizard Lips' displays rosettes of dark green variable to a lighter green, overlaid with reticulations of bright pearl white.
2. *Aloe* 'Crimson Dragon' exhibits a strongly variable, often truncately dentate to continuously dentate margin of crimson, whereas *Aloe* 'Lizard Lips' displays denticulate margins of translucent pale green to translucent white, recurved back towards the center of the rosette.
3. *Aloe* 'Crimson Dragon' morphologically differs from *Aloe* 'Lizard Lips' in that *Aloe* 'Crimson Dragon' produces rosettes of upswept, slightly recurved leaves, as compared with *Aloe* 'Lizard Lips', which exhibits a more horizontal morphology.

BRIEF DESCRIPTION OF THE PHOTOGRAPHS

The accompanying photograph in FIG. 1 illustrates in full color a typical plant of 'CRIMSON DRAGON' grown in a greenhouse (approximately 2000 foot candles of light) in Vista, Calif. This plant is approximately 10 months old, shown in a 1 gallon container.

Figure 2:
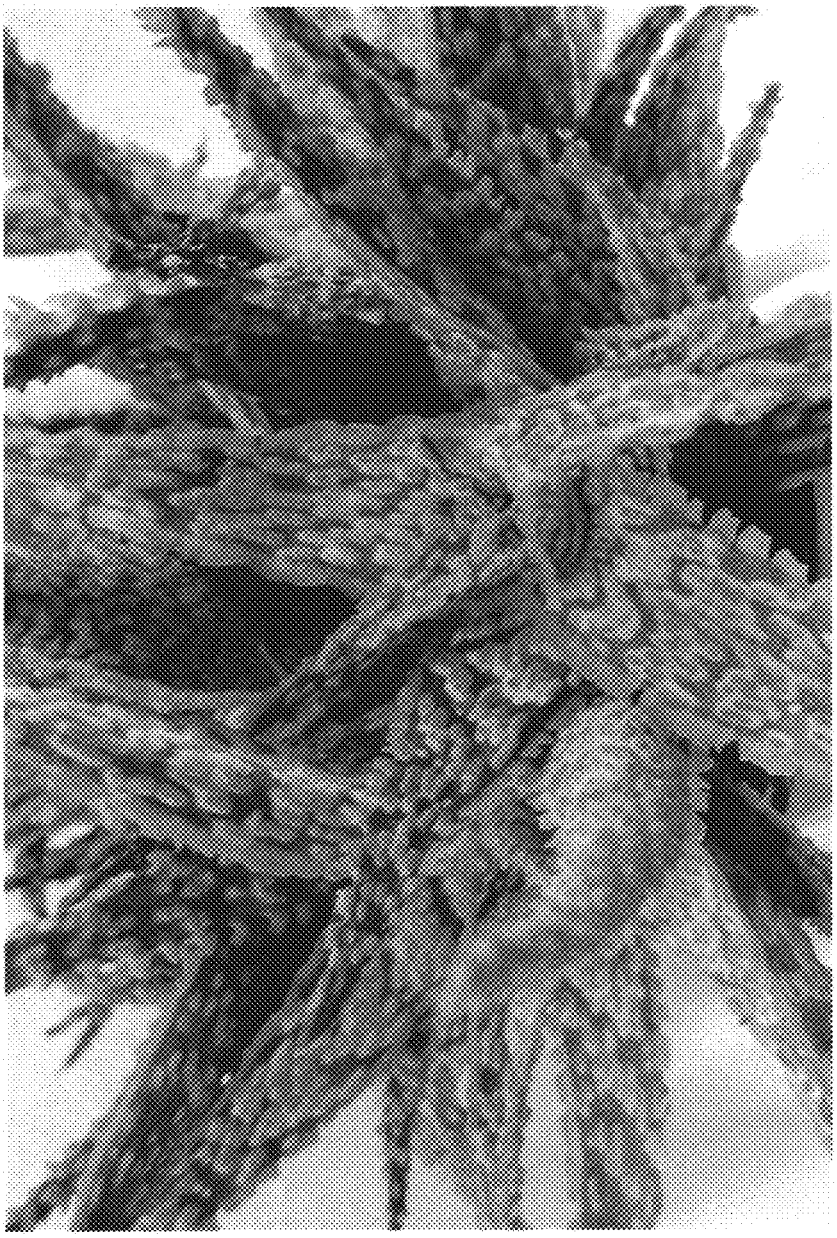

FIG. 2 illustrates a close-up view of the rosette. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 edition, except where general terms of ordinary dictionary significance are used. The following observations and measurements describe 'CRIMSON DRAGON' plants in a commercial greenhouse in Vista, Calif. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'CRIMSON DRAGON.'

Age of the plant described: About 1 year.

PROPAGATION

Time to initiate roots: Approximately 25 days at 22° C.

Root description: Fibrous. Brown, not accurately measured with the RHS chart.

Propagation method: Tissue culture.

PLANT

Growth habit: Multiple basal rosettes.

Container size: 5 inch.

Height: Approximately 18 cm to top of highest leaf.

Plant spread: Approximately 28 cm.

Growth rate: Moderate.

Branching characteristics: No branches, on average 8 to 10 basal rosettes.

FOLIAGE

Leaf:

*Arrangement.*—Rosette.

*Average length.*—Average range 7-11 cm.

*Average width.*—3 cm at base, widest point.

*Average thickness.*—About 2.5 to 3.0 mm at thickest.

*Shape of blade.*—Deltoid.

*Apex.*—Acute, with a sharp dentation.

*Base.*—Clasping.

*Margin.*—Irregularly occurring flattened, hard dentations. Dentations about 3 mm deep and 5 to 7 mm long.

*Texture of top surface.*—Non-pubescent scabrous. Oblong scabrous projections about 1 to 2 mm high, 3 to 5 mm long, 1-2 mm wide.

*Texture of bottom surface.*—Non-pubescent scabrous. Oblong scabrous projections about 1 to 2 mm high, 3 to 5 mm long, 1-2 mm wide.

*Quantity of leaves.*—Average range of about 6 to 9 per rosette.

*Color.*—Young foliage upper side: Near RHS Green 137A with oblong scabrous projections colored near Red 39A. Margin near Red 39A. Young foliage under side: Near RHS Green 137A with oblong scabrous projections colored near Red 39A. Margin near Red 39A. Mature foliage upper side: Near RHS Green 137A with oblong scabrous projections colored near Red 47D. Margin near Red 47D. Mature foliage under side: Near RHS Green 137A with oblong scabrous projections colored near Red 47D. Margin near Red 47D.

*Venation.*—Linear. Color: Indistinguishable from leaf blade.

FLOWER

Not observed to date.

OTHER CHARACTERISTICS

Seeds and fruits: Not observed to date.

Temperature tolerance: Tolerates temperatures from approximately 28° C. to 0° C.

Disease/pest resistance: Exhibited resistance to the *Eriophyid* mite (*Aloe* mite).

What is claimed is:

1. A new and distinct cultivar of *Aloe* plant named 'CRIMSON DRAGON' as herein illustrated and described.

* * * * *